United States Patent [19]

Fait et al.

[11] Patent Number: 4,699,806

[45] Date of Patent: Oct. 13, 1987

[54] METHOD OF PRODUCING FLUORIDE-SENSITIVE DIAPHRAGMS

[75] Inventors: Martin Fait, Berlin; Thomas Günther, Mühlhausen; Peter Janietz, Berlin; Werner Moritz, Berlin; Lothar Müller, Berlin; Hans Wellner, Schwarzenberg, all of German Democratic Rep.

[73] Assignee: Veb Waschgerätewerk Schwarzenberg, Schwarzenberg, German Democratic Rep.

[21] Appl. No.: 763,359

[22] Filed: Aug. 7, 1985

[30] Foreign Application Priority Data

Aug. 10, 1984 [DD] German Democratic Rep. .................................... 2661606

[51] Int. Cl.[4] .............................................. B05D 5/12
[52] U.S. Cl. .............................. 427/126.1; 204/192.1; 204/192.15; 427/248.1; 427/255
[58] Field of Search ...................... 427/248.1, 255, 87, 427/255.2, 58, 419.1, 126.1, 126.2; 204/192 SP, 192 R, 192 C, 192 D

[56] References Cited

U.S. PATENT DOCUMENTS

| 3,034,924 | 5/1962 | Kraus et al. | 427/255 |
| 3,147,132 | 9/1964 | Geffcken | 427/58 |
| 4,112,157 | 9/1978 | Krueger et al. | 427/255 |
| 4,146,309 | 3/1979 | Singh et al. | 427/126.1 |

FOREIGN PATENT DOCUMENTS

| 44-8007 | 4/1969 | Japan | 427/255.2 |
| 474576 | 9/1975 | U.S.S.R. | 427/255 |

OTHER PUBLICATIONS

Phahle et al, "Dielectric Properties of R.F. Sputtered Thin Aluminium Fluoride Films", Thin Solid Films, vol. 38, pp. 73–81, 1976.

MacDonald and Toth, *The Development of Fluoride—Sensitive Membrane Electrodes*, Part I., 1967, pp. 99–106.

Fjeldy and Nagy, *Fluoride Electrodes with Reversible Solid-State Contacts*, 1979, pp. 1299–1303.

Van Der Spiegel, Lauks, Chan, and Babic, *The Extended Gate Chemically Sensitive Field Effect Transistor as Multi-Species Microprobe*, 1983, pp. 291–298.

*Primary Examiner*—Sadie L. Childs
*Attorney, Agent, or Firm*—Michael J. Striker

[57] ABSTRACT

A method of manufacturing diaphragms which are sensitive to fluoride ions, by depositing a poly-crystalline thin layer of difficulty soluble fluoride of 20 nm to 5,000 nm thick by means of sputtering or vaporization onto a substrate at temperatures of above 280° C.

7 Claims, No Drawings

METHOD OF PRODUCING FLUORIDE-SENSITIVE DIAPHRAGMS

BACKGROUND OF THE INVENTION

The present invention pertains to a method of manufacturing fluoride-sensitive diaphragms which are employed as ion-sensitive electrodes in electro-analytic measuring practice.

Ion-sensitive electrodes have been widely known in electroanalysis for the determination of the amounts of ions. Various ion-sensitive electrodes have been developed during last years for detecting a great number of various ions.

In addition to known glass electrodes, $LaF_3$-monocrystal electrodes have also shown very good sensitivity, high selectivity and stability.

A non-porous diaphragm of difficultly soluble metal fluorides has been disclosed, for example in German Pat. No. 1,598,895.

At the present time, only monocrystal structures of $LaF_3$ with various dopings are used as fluoride-sensitive diaphragms. Due to high resistance of $LaF_3$ a doping has been necessary for monocrystal electrodes to improve conductivity in general (with Europium fluoride). The reduction of thickness of the diaphragm to reduce resistance has, however, failed up to now and led to non-satisfactory mechanical stability.

To use a $LaF_3$-monocrystal electrode, a monocrystal has been up till now glued into a tube of non-conductive material. An electrolyte solution containing fluoride ions was fed into that tube and an electric contact was provided between the electrolyte and a reference electrode. The utilization of such internal reference solution made the manufacture of electrodes difficult and has been often a cause for defects in the electrodes.

The manufacture of monocrystal electrodes has been very expensive which led to high costs of the electrodes.

Tests have been conducted to overcome deficiencies of $LaF_3$-monocrystals. It has been proposed, for example, to embed $LaF_3$ into a matrix of rubber, as disclosed in A. M. G. MacDonald, K. Toth, Anal. Chem. Acta 41, 99, 1968.

The utlization of $LaF_3$-stampings and an electrochemical production of $LaF_3$ have been disclosed by G. Uhlmann, Dissertation A, LEUNA, Merseburg, 1981.

All above described proposals were not carried through because sensitivity and long-time stability of monocrystal electrodes were insufficient. Tests for a drain of potential from a $LaF_3$ monocrystal have been carried out with an Ag/Ag F-contact. (T. A. Fjeldly, K. Nagy, J. Electrochem. Soc. 127, 1299, 1980). The manufacture of the contact by melting in inert gas has been, however, very expensive and this could not overcome high costs of the improved $LaF_3$-monocrystal.

Research has been conducted, which showed that, in order to avoid the above disadvantages, poly-silicon-conductive paths connected with the gate of the field-effect transistor have been coated with $LaF_3$, whereby the whole structure up to the fluoride-sensitive area has been coated with photo varnish (see J. van der Spiegel, u.a., "Sensors and Actuators", 4, 291, 1983).

The disadvantages of this technical solution are an extremely large potential drift which practically did not permit the use of such electrodes and also insufficient sensitivity in an ion analysis.

SUMMARY OF THE INVENTION

It is an object of the present invention to provide an improved method of manufacturing fluoride-sensitive diaphragms.

It is another object of this invention to provide a method by which costs of electrodes or diaphragms would be substantially reduced.

It is yet another object of the invention to provide a method of producing diaphragms which would be used for a fluoride ion-analysis, without inner reference solutions.

These and other objects of this invention are attained by a method of producing fluoride ion-sensitive diaphragms for ion-sensitive electrodes to be used for analysis of $F^-$-ions, comprising the steps of providing a substrate formed of metal, salts of this metal, semiconductive or insulation material, or of a multi-layer structure; and depositing onto said substrate at substrate temperatures of above 200° C. a layer of difficultly soluble fluoride by thermal vaporization or HF-sputtering to obtain polycrystalline layer of the thickness of 20 nm–5,000 nm.

The thickness of the deposited layer may be between 150 nm and 350 nm.

The temperatures of the substrate may be between 280° C. and 350° C. in said depositing step.

The depositing step may be carried out with a vaporization speed which is not greater than 0.5 $nm/S^{-1}$.

DETAILED DESCRIPTION OF THE INVENTION

The present invention is based on the method of depositing thin conductive layers onto metal substrates by vaporization or HF sputtering. Polycrystalline difficultly soluble fluorides, particularly fluorides of lanthanide series or their mixtures, are deposited by thermal vaporization or H-F sputtering in form of a thin layer or coating onto a suitable substrate.

The stable results and best analysis limits for $F^-$-ions can be obtained by the utilization of $LaF_3$. Particularly advantageous in the method proposed herein is the fact that due to a very small thickness of the fluoride layer, deposited by vaporization or sputtering, in contrast to monocrystal electrodes, no doping for improving conductivity is required.

The thickness of the layer of the ion-sensitive diaphragm is in the range from 20 nm to 5,000 nm because no pore-free structures can be obtained for thinner layers, and thereby the producing of mixing potentials is possible.

The optimal temperature of the substrate to which the fluoride coating is applied for producing the diaphragm is from above 280° C.

A great number of various materials can be used for substrates. These materials must have, however, outer surfaces of high qualities. The medium rough depth of the substrate should not exceed 50 nm in order to ensure compactness of the diaphragm and prevent potential instability.

A boundary layer for the diaphragm can be formed of metal, salts of this metal, semiconductors or insulation coatings. The substrate can be also made as a multiple-layer structure of these materials.

For a satisfactory functin of the diaphragm the speed of vaporization is an important parameter. With vaporization speeds below 0.5 $nm/S^{-1}$ good results in reproducible fashion can be achieved. It has been discovered that the diaphragm manufactured under such conditions, which is undoubtedly polycrystalline, has the sensitivity which completely corresponds to that of a monocrystal electrode.

By the method of this invention a fluoride-sensitive diaphragm is produced, which requires no inner reference solution for a potential drain and makes it possible to measure a potential change on the phase terminals of the diaphragm for detecting solutions via the substrate.

The disguise of the drain of potential is easy to realize because only rigid components are available.

If a metal or other conductive compound is provided as a boundary layer for the diaphragm the activity of fluoride ions in the solution being tested is determined directly by the measurement of the voltage between a series reference electrode—the solution being tested—diaphragm—substrate by means of a single high-resistance voltmeter.

The diaphragms manufactured by the method of this invention have sensitivity of 57 mV per decade up to a fluoride ion-concentration smaller than $10^{-5}$ mol/liter. The selectivity of such diaphragms corresponds to that of the $LaF_3$-monocrystal. The long-time stability is characterized by a very small potential drift.

The method of making fluoride ion-sensitive diaphragms of this invention ensures an economical manufacture of such diaphragms, suitable for mass production and ensures the use of such diaphragms for a continual and/or discontinual analysis of fluoride ions.

EXAMPLE 1

A polished Si-disc (110) coated with a layer of gold of 100 nm is then coated with a 270 nm-thick layer of $LaF_3$ at the temperature of 280° C., this layer being applied to the gold coating by thermal vaporization at a vaporization speed of 0.5 $nm/S^{-1}$.

A piece of the size $6\times 6$ mm$^2$ is then cut off and the gold layer is connected with a feedback contact of a brass wire by means of varnish of conductive silver.

This arrangement is glued to a pretreated cylinder of TEFLON with epoxide resin so that only the $LaF_3$-layer remains free. The electrode can be used in solutions with various fluoride ion-contents. The feedback contact would be connected with the high impedance voltmeter and the measuring circuit by a standard calomeric electrode which has been immersed in the similar solution.

Following measure values were obtained:

| Concentration $F^-$ (mol/liter) | Reading in mV |
| --- | --- |
| $1.10^{-1}$ | $-27$ |
| $1.10^{-2}$ | $+23$ |
| $1.10^{-3}$ | $+86$ |
| $1.10^{-4}$ | $+145$ |
| $1.10^{-5}$ | $+201$ |

EXAMPLE II

A Si-disc is coated with a silver layer of 100 nm. The thermal vaporization is carried out at the temperature of 320° C. and with vaporization speed of 0.2 $nm/S^{-1}$ to deposit a $LaF_3$-layer of 100 nm onto the silver coating. The such obtained piece is connected to the feedback contact in the same manner as that for Example I and the diaphragm is used for measuring the content of $F^-$ in solutions.

The measure values obtained from use of the diaphragm produced by the method in Example II are as follows:

| Concentration $F^-$ (mol/liter) | Reading in mV |
| --- | --- |
| $1.10^{-1}$ | $+88$ |
| $1.10^{-2}$ | $+142$ |
| $1.10^{-3}$ | $+199$ |
| $1.10^{-4}$ | $+257$ |
| $1.10^{-5}$ | $+313$ |

A potential drift that occurred over the period of six months was 0.1 mV per day.

It will be understood that each of the elements described above, or two or more together, may also find a useful application in other types of methods of manufacturing fluoride ion-sensitive diaphragms differing from the types described above.

While the invention has been illustrated and described as embodied in a method of producing fluoride ion-sensitive diaphragms, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of producing fluoride ion-sensitive diaphragms for particular use in ion-sensitive electrodes to be used for analysis of $F^-$-ions, comprising the steps of providing a substrate formed of metal, salts of this metal, semiconductive or insulation material, or a multi-layer structure; and depositing immediately onto said substrate at substrate temperatures higher than 200° C. a layer of difficulty soluble fluoride by thermal vaporization or HF-sputtering to obtain on said substrate a polycrystalline layer of the thickness of 20 nm to 5,000 nm.
crystalline layer of the thickness of 20 nm to 5,000 nm.

2. The method as defined in claim 1, wherein said fluoride is of lanthanide series or mixtures with other fluorides.

3. The method as defined in claim 1, wherein said difficultly soluble fluoride is $LaF_3$.

4. The method as defined in claim 1, wherein the thickness of said deposited layer is between 150 nm and 350 nm.

5. The method as defined in claim 1, wherein said temperatures are maintained between 280° C. and 350° C.

6. The method as defined in claim 1, wherein a material used for the substrate has an upper face of high qualities with a medium coarse depth smaller than 50 nm.

7. The method as defined in claim 1, wherein said depositing step is carried out with a vaporization speed which is not greater than 0.5 $nm/S^{-1}$.

* * * * *